US006586379B1

(12) United States Patent
Seipel

(10) Patent No.: US 6,586,379 B1
(45) Date of Patent: Jul. 1, 2003

(54) SYNDET SOAP BARS COMPRISING OLEFIN SULFONATE

(75) Inventor: Werner Seipel, Hilden (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/806,625

(22) PCT Filed: Sep. 23, 1999

(86) PCT No.: PCT/EP99/07081

§ 371 (c)(1), (2), (4) Date: Jun. 4, 2001

(87) PCT Pub. No.: WO00/20551

PCT Pub. Date: Apr. 13, 2000

(30) Foreign Application Priority Data

Oct. 2, 1998 (DE) ........................................ 198 45 456

(51) Int. Cl.[7] ................................................ A61K 7/50

(52) U.S. Cl. ....................... 510/155; 510/151; 510/152; 510/156; 510/470; 510/474

(58) Field of Search ................................ 510/155, 151, 510/152, 470, 156, 474

(56) References Cited

U.S. PATENT DOCUMENTS

| | | | |
|---|---|---|---|
| 4,172,887 | A | 10/1979 | Vanlerberghe et al. |
| 5,262,079 | A | 11/1993 | Kacher et al. |
| 5,374,716 | A | 12/1994 | Biermann et al. |
| 5,540,854 | A | 7/1996 | Fair et al. |
| 5,576,425 | A | 11/1996 | Hill et al. |
| 5,705,462 | A | 1/1998 | Hormes et al. |
| 5,712,235 | A | 1/1998 | Nieendick et al. |
| 5,981,452 | A | 11/1999 | Schrader et al. |
| 6,140,302 | A | 10/2000 | Lueder et al. |

FOREIGN PATENT DOCUMENTS

| | | |
|---|---|---|
| DE | 1165 574 | 3/1964 |
| DE | 20 24 051 | 12/1971 |
| DE | 43 31 297 | 3/1995 |
| DE | 43 37 031 | 5/1995 |
| DE | 43 40 015 | 6/1995 |
| DE | 195 45 136 | 4/1997 |
| DE | 197 10 152 | 9/1998 |
| EP | 0 227 321 | 7/1987 |
| EP | 0 301 298 | 2/1989 |
| EP | 0 308 189 | 3/1989 |
| EP | 0 308 190 | 3/1989 |
| EP | 0 463 912 | 1/1992 |
| FR | 2252840 | 6/1975 |
| GB | 962919 | 8/1961 |
| GB | 1333475 | 5/1971 |
| GB | 2 316 087 | 2/1998 |
| WO | WO 90/03977 | 4/1990 |
| WO | WO 99/10468 | 3/1999 |
| WO | WO 99/10469 | 3/1999 |

OTHER PUBLICATIONS

Tuvell, et al., "AOS—An Anionic Surfactant System: Its Manufacture, Composition, Properties, and Potential Application," J. AM. Oil Chemists' Soc., vol. 55, pp. 70–80, (Jan. 1978).

Falbe, et al., "Surfactants in Consumer Products," Springer Verlag, pp. 54–124, Berlin, 1987.

Falbe, et al., "Catalysts, Surfactants and Mineral Oil Additives," Thieme Verlag, pp. 123–217, Stuttgart, 1978.

Todd, et al., "Volatile Silicone Fluids for Cosmetic Formulations, Cosmetics and Toiletries," vol. 29, pp. 29–32, (Jan. 1976).

Tronnier, et al., "Experimentelle Untersuchungen zur Wirkungsweise Aluminiumhaltiger Antiperspiranzien,"J, Soc. Cosm. Chem., vol. 24, pp. 281–290, 1973.

Graham, et al., "Inhibition of the Mitochondrial Oxidation of Octanoate by Salicylic Acid and Related Compounds," J. Pharm. Pharmcol., vol. 26, pp. 531–534, Hoechst AG, Frankfurt, 1975.

"Kosmetische Färbemittel," Farbstoffkommission der Deutschen Forschungsgemeinschaft, Verlag Chemie, pp. 81–106, 1984.

*Primary Examiner*—Necholus Ogden

(74) *Attorney, Agent, or Firm*—John E. Drach; Steven J. Trzaska

(57) ABSTRACT

A soap bar composition containing: (a) an alkyl/alkenyl oligoglycoside; (b) an olefin sulfonate; and (c) a starch component, and wherein the soap bar composition is subtantially free of free fatty acids or their salts.

11 Claims, No Drawings

SYNDET SOAP BARS COMPRISING OLEFIN SULFONATE

BACKGROUND OF THE INVENTION

This invention relates to fatty-acid-free syndet bar soaps containing alkyl and/or alkenyl oligoglycosides, olefin sulfonates and starch.

Bar soaps play an important part in personal hygiene. Today, bar soaps are industrially produced by continuous saponification of free fatty acids with alkalis, concentration of the basic soaps and spray drying. A distinction is drawn between true alkali soaps, which contain only fatty acid salts and optionally free fatty acids, and so-called "combination bars", i.e. bar soaps which—in addition to fatty acid salts—contain other synthetic surfactants, generally fatty alcohol ether sulfates or fatty acid isethionates. By contrast, a special position is occupied by so-called "syndet bars" which, apart from impurities, are free from fatty acid salts and contain only synthetic surfactants.

In Germany alone, several million bars of soap for personal hygiene are sold annually. However, the commercial requirements which these mass consumption articles are expected to satisfy are becoming increasingly more stringent. Bar soaps are required not only to clean, but also to care for the skin, i.e. to prevent the skin from drying out, to "refat" the skin and to protect it against outside influences. The soap is of course expected to be particularly compatible with the skin, but at the same time to produce an abundant and creamy foam in use and to have a pleasant feeling on the skin. In this connection, manufacturers of bar soaps are constantly looking for new ingredients which satisfy these increased requirements.

In recent years, alkyl glucosides have acquired significance as new nonionic surfactants because they behave like anionic surfactants in many respects, for example in their foaming power, and at the same time show extremely high ecological and dermatological compatibility. Accordingly, it was logical to experiment with such surfactants in connection with bar soaps. For example, toilet soaps containing 1 to 20% by weight of alkyl polyglucosides and preferably 55 to 66% by weight of soap as builder are known from European patent application EP 0 463 912 A (Colgate). Toilet soaps containing mild surfactants, including for example those of the alkyl polyglucoside type, are known from EP 0 227 321 A2, EP 0 308 189 B1 and EP 0 308 190 B1 (Procter & Gamble). In addition, DE 43 31 297 A1 and DE 43 37 031 A1 (Henkel) describe fatty-acid-salt-containing combination bars in which small quantities of alkyl polyglucosides are present. Finally, DE 1945136 C1 describes syndet bar soaps containing 5 to 25% by weight of alkyl and/or alkenyl oligoglycosides and 5 to 40% by weight of starch. However, the bar soaps obtainable in accordance with the teaching of the prior art do not always develop enough foam and, in addition, are unsatisfactory in regard to foam consistency and, in particular, the feeling they have on the skin. In addition, if free fatty acids are used as refatting agents, extremely serious corrosion problems can occur in manufacturing equipment.

Accordingly, the problem addressed by the present invention was to provide syndet soaps which would be free from the disadvantages described above. A particular factor to be taken into consideration in this regard was that the new bar soap compositions would also have to lend themselves to production on an industrial scale, i.e. they would be expected, for example, to show adequate, but not excessive moldability and would not have any tendency to form cracks on drying.

DESCRIPTION OF THE INVENTION

The present invention relates to syndet soaps containing
(a) alkyl and/or alkenyl oligoglycosides,
(b) olefin sulfonates and
(c) starch.

It has surprisingly been found that bar soaps with improved foaming behavior and an optimized feeling on the skin can be produced in the absence of fatty acids or fatty acid salts providing mixtures of alkyl and/or alkenyl oligoglycosides and olefin sulfonates, preferably in water-free form, are used as the surfactant component and starch is used as builder. The invention includes the observation that the mixtures are also eminently suitable for the industrial production of bar soaps, i.e. they are stable during storage in air, substantially non-hygroscopic and moldable and do not crack on drying.

Alkyl and/or Alkenyl Oligoglycosides

Alkyl and alkenyl oligoglycosides are known nonionic surfactants corresponding to formula (I):

$$R^1O\text{—}[G]_p \qquad (I)$$

in which $R^1$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP 0 301 298 A1 and WO 90/03977 are cited as representative of the extensive literature available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ cocoalcohol with a DP of 1 to 3 are preferred.

Olefin Sulfonates

The syndet soaps according to the invention contain anionic surfactants obtainable by methods known per se as a further component. Olefin sulfonates are preferably obtained by addition of $SO_3$ onto olefins corresponding to formula (II):

$$R^2—CH═CH—R^3 \quad (II)$$

in which $R^2$ and $R^3$ independently of one another represent H or alkyl groups containing 1 to 20 carbon atoms, with the proviso that $R^2$ and $R^3$ together contain at least 6 and preferably 10 to 16 carbon atoms. Particulars of their production and use can be found in a synoptic article published in J. Am. Oil. Chem. Soc. 55, 70 (1978). Internal olefin sulfonates may be used although α-olefin sulfonates which are obtained $R^2$ or $R^3$ is hydrogen are preferably used. Typical examples of the olefin sulfonates used are the sulfonation products obtained by reacting $SO_3$ with 1-, 2-butene, 1-, 2-, 3-hexene, 1-, 2-, 3-, 4-octene, 1-, 2-, 3-, 4-, 5-decane, 1-, 2-, 3-, 4-, 5-, 6-dodecene, 1-, 2-, 3-, 4-, 5-, 6-, 7-tetradecene, 1-, 2-, 3-, 4-, 5-, 6-, 7-, 8-hexadecene, 1-, 2-, 3-, 4-, 5-, 6-, 7-, 8-, 9-octadecene, 1-, 2-, 3-, 4-, 5-, 6-, 7-, 8-, 9-, 10-eicosene and 1-, 2-, 3-, 4-, 5-, 6-, 7-, 8-, 9-, 10- and 11-docosene. The sulfonation is followed by a neutralization step, after which the olefin sulfonate is present in the mixture as an alkali metal, alkaline earth metal, ammonium, alkyl ammonium, alkanolammonium or glucammonium salt and preferably as a sodium salt. It is possible to use both paste-form aqueous olefin sulfonates, preferably at a pH value of 7 to 10, and also water-free products, preferably in the form of granules obtained by conventional spray drying, drying in a thin-layer evaporator (flash dryer, ctf. DE 19710152 C1, Henkel KGaA) or in a fluidized-bed dryer (SKET dryer).

Starch

It is particularly preferred to use wheat and/or corn starch which may be used in untreated form or preferably in digested, i.e. partly hydrolyzed, form. In one particular embodiment of the invention, compounds of alkyl glucosides, olefin sulfonates and starch are produced by subjecting aqueous slurries of the three components to drying with superheated steam, as described for example in German patent application DE 43 40 015 A1 (Henkel), to which reference is hereby specifically made. However, drying may also be carried out by other processes, for example in a horizontally arranged thin-layer evaporator (flash dryer") or in a fluidized-bed dryer (SKET dryer).

Surfactants

The syndet soaps according to the invention may also contain anionic, nonionic, cationic and/or amphoteric or zwitterionic surfactants as constituents which normally make up about 50 to 99% by weight and preferably 70 to 90% by weight of the syndet soaps. Typical examples of anionic surfactants are alkylbenzenesulfonates, alkanesulfonates, olefin sulfonates, alkylether sulfonates, glycerol ether sulfonates, α-methyl ester sulfonates, sulfofatty acids, alkylsulfates, fatty alcohol ether sulfates, glycerol ether sulfates, fatty acid ether sulfates, hydrbxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates, acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow homolog distribution. Typical examples of cationic surfactants are quaternary ammonium compounds and esterquats, more particularly quaternized fatty acid trialkanolamine ester salts. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside und Mineralöladditive (Catalysts, Surfactants and Mineral Oil Additives)", Thieme Verlag, Stuttgart, 1978, pages 123–217.

Syndet Bar Soaps

Syndet bar soaps with a particularly favorable feeling on the skin and a creamy foam contain the ingredients in the following quantities:

(a) 5 to 25 and preferably 10 to 20% by weight of alkyl and/or alkenyl oligoglycosides, (b) 5 to 50 and preferably 20 to 40% by weight of olefin sulfonates, (c) 5 to 40 and preferably 15 to 30% by weight of starch and (d) 0 to 20 and preferably 5 to 10% by weight of other surfactants, with the proviso that the quantities add up to 100% by weight.

Other preferred constituents of the syndet bar soaps according to the invention are fatty alcohols and polyethylene glycol ethers. Typical examples of suitable fatty alcohols are lauryl alcohol, myristyl alcohol, cetearyl alcohol, stearyl alcohol and isostearyl alcohol. Suitable polyethylene glycol ethers are those which have an average molecular weight in the range from 5,000 to 20,000 dalton.

Commercial Applications

The syndet bar soaps according to the invention are substantially free from fatty acids or fatty acid salts, i.e. the content of these substances is below 0.5% by weight. Nevertheless, the soaps produce a surprisingly large amount of a particularly creamy foam in use and, in addition, have a particularly pleasant feeling on the skin.

Auxiliaries and Additives

The syndet soaps may contain oils, emulsifiers, superfatting agents, consistency providers, thickeners, polymers, silicone compounds, fats, waxes, stabilizers, waxes, biogenic agents, deodorizers, swelling agents, pigments, antioxidants, preservatives, hydrotropes, perfume oils, dyes and the like as further auxiliaries and additives.

Suitable oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more particularly 2-ethyl hexanol, esters of hydroxycarboxylic acids with linear or branched $C_{6-22}$ fatty alcohols, more particularly Dioctyl Malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons.

Suitable emulsifiers are, for example, nonionic surfactants from at least one of the following groups:

(1) products of the addition of 2 to 30 moles of ethylene oxide and/or 0 to 5 moles of propylene oxide onto linear fatty alcohols containing 8 to 22 carbon atoms, onto fatty acids containing 12 to 22 carbon atoms and onto alkylphenols containing 8 to 15 carbon atoms in the alkyl group;

(2) $C_{12/18}$ fatty acid monoesters and diesters of products of the addition of 1 to 30 moles of ethylene oxide onto glycerol;

(3) glycerol monoesters and diesters and sorbitan monoesters and diesters of saturated and unsaturated fatty acids containing 6 to 22 carbon atoms and ethylene oxide adducts thereof;

(4) alkyl mono- and oligoglycosides containing 8 to 22 carbon atoms in the alkyl group and ethoxylated analogs thereof;

(5) adducts of 15 to 60 moles of ethylene oxide with castor oil and/or hydrogenated castor oil;

(6) polyol esters and, in particular, polyglycerol esters such as, for example, polyglycerol polyricinoleate, polyglycerol poly-12-hydroxy-stearate and polyglycerol dimerate isostearate. Mixtures of compounds from several of these classes are also suitable;

(7) products of the addition of 2 to 15 moles of ethylene oxide onto castor oil and/or hydrogenated castor oil;

(8) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(9) mono-, di- and trialkyl phosphates and mono-, di- and/or tri-PEG-alkyl phosphates and salts thereof;

(10) wool wax alcohols;

(11) polysiloxane/polyalkyl polyether copolymers and corresponding derivatives;

(12) mixed esters of pentaerythritol, fatty acids, citric acid and fatty alcohol according to DE-PS 1165574 and/or mixed esters of fatty acids containing 6 to 22 carbon atoms, methyl glucose and polyols, preferably glycerol or polyglycerol, and

(13) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known, commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051.

$C_{8/18}$ alkyl mono- and oligoglycosides, their production and their use as surfactants are known from the prior art. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

Zwitterionic surfactants may also be used as emulsifiers. Zwitterionic surfactants are surface-active compounds which contain at least one quaternary ammonium group and at least one carboxylate and one sulfonate group in the molecule. Particularly suitable zwitterionic urfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. Besides the ampholytic emulsifiers, quaternary emulsifiers may also be used, those of the esterquat type, preferably methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

Suitable consistency providers are primarily fatty alcohols and hydroxyfatty alcohols containing 12 to 22 carbon atoms and preferably 16 to 18 carbon atoms and also partial glycerides, fatty acids or hydroxyfatty acids. A preferred consistency provider is a combination of these substances with alkyl oligoglucosides and/or fatty acid-N-methyl glucamides of the same chain length and/or polyglycerol-12-hydroxystearates. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau GmbH), quaternized wheat polypeptides, polyethyleneimine, cationic silicone polymers such as, for example, Amidomethicone, copolymers of adipic acid and dimethylaminohydroxypropyl diethylenetriamine (Cartaretine®, Sandoz AG), copolymers of acrylic acid with dimethyl diallyl ammonium chloride (Merquat® 550, Chemviron), polyaminopolyamides as described, for example, in FR 2 252 840 A and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, USA, quaternized ammonium salt polymers such as, for example, Mirapol® A-15, Mirapol® AD-1, Mirapol® AZ-1 of Miranol, USA.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. In addition, a detailed review of suitable liquid silicones was published by Todd et al. in Cosm. Toil. 91, 27 (1976).

Typical examples of fats are glycerides while suitable waxes are inter alia beeswax, carnauba wax, candelilla wax, montan wax, paraffin wax, hydrogenated castor oils, fatty acid esters solid at room temperature or microwaxes optionally in combination with hydrophilic waxes, for example cetyl stearyl alcohol or partial glycerides. Metal salts of fatty acids such as, for example, magnesium, aluminium and/or zinc stearate or ricinoleate may be used as stabilizers.

In the context of the invention, biogenic agents are, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Suitable deodorizers are, for example, antiperspirants, such as aluminium chlorohydrates. These antiperspirants are colorless hygroscopic crystals which readily deliquesce in air and which accumulate when aqueous aluminium chloride solutions are concentrated by evaporation. Aluminium chlorohydrate is used for the production of perspiration-inhibiting and deodorizing formulations and probably acts by partially blocking the sweat glands through the precipitation of proteins and/or polysaccharides [cf. J. Soc. Cosm. Chem. 24, 281 (1973)]. For example, an aluminium chlorohydrate which corresponds to the formula $[Al_2(OH)_5Cl].2.5H_2O$ and which is particularly preferred for the purposes of the invention is commercially available under the name of Locron® from Hoechst AG of Frankfurt, FRG [cf. J. Pharm. Pharmcol. 26, 531 (1975)]. Besides the chlorohydrates, aluminium hydroxylactates and acidic aluminium/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Henkel KGBA, Düsseldorf, FRG). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products. Examples of such antibacterial agents are chitosan, phenoxyethanol and chlorhexidine gluconate. 5-Chloro-2-(2,4-dichlorophenoxyyphenol, which is marketed under the name of Irgasan® by Ciba-Geigy of Basel, Switzerland, has also proved to be particularly effective.

In addition, hydrotropes, for example ethanol, isopropyl alcohol or polyols, may be used to improve flow behavior. Suitable polyols preferably contain 2 to 15 carbon atoms and at least two hydroxyl groups. Typical examples are

- glycerol;
- alkylene glycols such as, for example, ethylene glycol, diethylene glycol, propylene glycol, butylene glycol, hexylene glycol and polyethylene glycols with an average molecular weight of 100 to 1000 dalton;
- technical oligoglycerol mixtures with a degree of self-condensation of 1.5 to 10 such as, for example, technical diglycerol mixtures with a diglycerol content of 40 to 50% by weight;
- methylol compounds such as, in particular, trimethylol ethane, trimethylol propane, trimethylol butane, pentaerythritol and dipentaerythritol;
- lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive"). Suitable pigments are finely dispersed metal oxides and salts. Examples of suitable metal oxides are, in particular, zinc oxide and titanium dioxide and also oxides of iron, zirconium, silicon, manganese, aluminium and cerium and mixtures thereof. Silicates (talcum), barium sulfate or zinc stearate may be used as salts.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evemyl, iraldein gamma, phenylacetic acid, geranyl acetate, benzyl acetate, rose oxide, romillate, irony and floramate.

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular composition. The compositions may be produced by standard cold or hot methods, preferably by the phase inversion temperature method.

EXAMPLES

Bar soaps were produced on the basis of formulation 1 according to the invention and comparison formulations C1 and C2 and tested for their performance properties. The results are set out in Table 1 below.

TABLE 1

Compositions (% by weight) and properties of the bar soaps

| Composition and performance | 1 | C1 | C2 |
|---|---|---|---|
| Plantacare ® APG 1200 G Lauryl Glucoside | 15.0 | 15.0 | 15.0 |
| Witconate ® A06 Sodium C12/14 Olefin Sulfonate | 40.0 | 40.0 | — |
| Texapon ® K 12 Pulver Sodium Lauryl Sulfate | — | — | 40.0 |
| Paraffin oil (Mp. 54° C.) | 8.0 | 8.0 | 8.0 |
| Hydrenol ® DD Tallow Fatty Alcohol | 7.0 | 7.0 | 7.0 |
| Maisstärke RG 3452 Mainze Starch | 17.0 | — | 17.0 |
| Dextrose | — | 17.0 | — |
| Edenor ® HK 12–18 Coco Fatty Acids | 10.0 | 10.0 | 10.0 |
| Titane Dioxide | 1.0 | 1.0 | 1.0 |
| Water | | to 100 | |
| Feeling on the skin | ++ | + | ++ |
| Friction foam | +++ | ++ | + |
| Tendency to take up water | – | + | + |
| Hardness | + | + | – |
| Moldbility | ++ | + | – |
| Cracking after drying | – | + | Not determined |

The results show clear advantages for the formulation according to the invention in all the test criteria. Bar soaps containing olefin sulfonate, but dextrose instead of starch as builder (C1) are distinguished from Example 1 according to the invention by a poorer feeling on the skin, reduced foaming, a greater tendency to take up water, lower deformability and cracking after drying. If the olefin sulfonate in Example 1 is replaced by another anionic surfactant (in this case sodium lauryl sulfate) (C2), foaming is reduced even further and hygroscopic, soft and, accordingly, non-moldable bar soaps are obtained.

What is claimed is:

1. A soap bar composition comprising:

(a) from about 5 to 25% by weight of an alkyl/alkenyl oligoglycoside;

(b) from about 5 to 50% by weight of an olefin sulfonate; and (c) from about 5 to 40% by weight of a starch component.

2. The composition of claim 1 wherein the olefin sulfonate is derived by adding $SO_3$ onto an olefin corresponding to formula (II):

$$R^2—CH═CH—R^3 \qquad (II)$$

wherein $R^2$ and $R^3$, independently of one another represent hydrogen or an alkyl group having from 1 to 20 carbon atoms, with the proviso that $R^2$ and $R^3$ together contain at least 6 carbon atoms.

3. The composition of claim 1 wherein the starch component is selected from the group consisting of wheat starch, corn starch, and mixtures thereof.

4. The composition of claim 1 wherein the composition contains less than 0.5% by weight, based on the weight of the composition of a free fatty acid or its salt.

5. The composition of claim 1 wherein the alkyl/alkenyl oligoglycoside is present in the composition in an amount of from 10 to 20% by weight, based on the weight of the composition.

6. The composition of claim 1 wherein the starch component is present in the composition in an amount of from 20 to 40% by weight, based on the weight of the composition.

7. The composition of claim 1 wherein the starch component is present in the composition in an amount of from 15 to 30% by weight, based on the weight of the composition.

8. A process for making a soap bar comprising:

(a) from about 5 to 25% by weight of providing an alkyl/alkenyl oligoglycoside;

(c) from about 5 to 50% by weight of providing an olefin sulfonate;

(d) from about 5 to 40% by weight of providing a starch component;

(e) combining (a)–(d) to form the soap composition; and (f) casting the soap composition into a bar which is substantially free of free fatty acids or their salts.

9. The process of claim 8 wherein the olefin sulfonate is derived by adding $SO_3$ onto an olefin corresponding to formula (II):

$$R^2—CH=CH—R^3 \quad (II)$$

wherein $R^2$ and $R^3$, independently of one another represent hydrogen or an alkyl group having from 1 to 20 carbon atoms, with the proviso that $R^2$ and $R^3$ together contain at least 6 carbon atoms.

10. The process of claim 8 wherein the starch component is selected from the group consisting of wheat starch, corn starch, and mixtures thereof.

11. The process of claim 8 wherein the composition contains less than 0.5% by weight, based on the weight of the composition of a free fatty acid or its salt.

* * * * *